(12) United States Patent  
Kodama

(10) Patent No.: US 10,857,338 B2  
(45) Date of Patent: Dec. 8, 2020

(54) MICRONEEDLE

(71) Applicant: TOPPAN PRINTING CO., LTD., Tokyo (JP)

(72) Inventor: Yoshihiro Kodama, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 138 days.

(21) Appl. No.: 16/003,459

(22) PCT Filed: Jan. 19, 2017

(86) PCT No.: PCT/JP2017/001815  
§ 371 (c)(1),  
(2) Date: Jun. 8, 2018

(87) PCT Pub. No.: WO2017/135060  
PCT Pub. Date: Aug. 10, 2017

(65) Prior Publication Data  
US 2019/0022364 A1    Jan. 24, 2019

(30) Foreign Application Priority Data

Feb. 4, 2016 (JP) .................. 2016-019727

(51) Int. Cl.  
*A61M 37/00* (2006.01)  
*A61M 5/158* (2006.01)

(52) U.S. Cl.  
CPC ........ *A61M 37/0015* (2013.01); *A61M 37/00* (2013.01); *A61M 5/158* (2013.01);  
(Continued)

(58) Field of Classification Search  
CPC .............. A61M 37/0015; A61M 37/00; A61M 37/0076; A61M 37/0084;  
(Continued)

(56) References Cited

U.S. PATENT DOCUMENTS

| 2003/0050602 | A1* | 3/2003 | Pettis | ...................... A61M 5/46 604/117 |
| 2005/0049549 | A1* | 3/2005 | Wong | ................. A61B 10/0064 604/46 |

(Continued)

FOREIGN PATENT DOCUMENTS

| JP | 2005-021677 A | 1/2005 |
| JP | 2014-176765 A | 9/2014 |

OTHER PUBLICATIONS

English Translation of JP 2014-176765 (Year: 2014).*  
International Search Report with English language translation and Written Opinion issued in International Application No. PCT/JP2017/001815 dated Apr. 4, 2017.

*Primary Examiner* — Nathan R Price  
*Assistant Examiner* — Jacob Michael Lindsay  
(74) *Attorney, Agent, or Firm* — Foley & Lardner LLP

(57) ABSTRACT

A microneedle includes a base having a support surface, and a projection that protrudes from the support surface, the projection having a through hole that penetrates the projection in an extending direction of the projection. The projection includes a flow path expansion section which is configured to expand a communication path that communicates between an inner space of the through hole and a space surrounding the projection in response to an increase in pressure of a fluid flowing in the through hole.

18 Claims, 5 Drawing Sheets

(52) U.S. Cl.
CPC .............. *A61M 2037/003* (2013.01); *A61M 2037/0023* (2013.01); *A61M 2037/0038* (2013.01); *A61M 2037/0053* (2013.01)

(58) Field of Classification Search
CPC .... A61M 2037/0023; A61M 2037/003; A61M 2037/0038; A61M 2037/0053; A61M 2037/0061; A61M 5/31531; A61M 5/3295; A61M 5/3297; A61M 5/3298; A61M 5/3286; A61M 5/329; A61M 5/3291; A61M 2025/0042; A61M 2025/0093; A61M 2025/205; A61B 17/205; A01K 11/005
See application file for complete search history.

(56) References Cited

U.S. PATENT DOCUMENTS

| | | | |
|---|---|---|---|
| 2008/0200883 A1* | 8/2008 | Tomono | A61M 37/0015 604/272 |
| 2009/0093775 A1* | 4/2009 | Raju | A61M 37/0015 604/272 |
| 2011/0125101 A1* | 5/2011 | Koyama | A61F 11/004 604/239 |
| 2012/0296280 A1* | 11/2012 | Eum | A61M 37/0015 604/113 |
| 2015/0306363 A1* | 10/2015 | Meyer | A61M 37/0015 604/173 |

* cited by examiner

MICRONEEDLE

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2017/001815, filed on Jan. 19, 2017, which is based upon and claims the benefit of priority to Japanese Patent Application No. 2016-019727, filed on Feb. 4, 2016, the disclosures of which are all hereby incorporated herein by reference in their entireties.

BACKGROUND

Technical Field

The present invention relates to microneedles for transdermal administration.

Background Art

Microneedles are known to be used for administration of drugs such as vaccines into the body (for example, see PTL 1). Microneedles have a needle-shaped projection protruding from a surface of a base. The administration method using a microneedle is a technique of drug administration by which a drug is delivered intradermally through a hole created in the skin by a projection pierced into the skin. The projection has a length that does not reach nerve cells in the dermis layer of the skin. Accordingly, the administration method using a microneedle reduces pain caused by puncturing the skin compared with subcutaneous drug administration using a normal injection needle. Further, in the drug administration using a microneedle, a drug is delivered into the intradermal layer of the skin which is abundant in antigen presenting cells. Accordingly, there is a possibility that the dose of the drug can be reduced compared with subcutaneous drug administration.

In one of the drug administration methods using a microneedle, a microneedle has a through hole that extends in an extending direction of the projection and penetrates the base and the projection such that a drug in liquid form, a liquid drug, is delivered intradermally through the through hole. Such a microneedle is, for example, attached to a syringe barrel for use as an injection needle. In drug administration, a plunger of the syringe barrel is pushed. Accordingly, a pressure is applied to the liquid drug filled in an outer cylinder of the syringe barrel so that the liquid drug is urged toward the projection. As a result, the liquid drug flows into the through hole, and is delivered intradermally as it exits the tip of the projection.

CITATION LIST

Patent Literature

[PTL 1] JP-2005-21677 A

SUMMARY OF THE INVENTION

Technical Problem

When the projection having a through hole is pierced into the skin, skin tissue may enter the through hole, which disturbs a flow of the liquid drug in the through hole. This may be one of the factors that disturb smooth administration of a drug by a microneedle.

Unlike subcutaneous injection by which the tip of the needle reaches the hypodermis, the tip of the projection of the microneedle is located in the intradermal layer of the skin during drug administration. Since the intradermal layer is rich with cells compared with the hypodermis and thus has an increased internal pressure, and the through hole of the projection has a small diameter compared with that of the through hole of typical injection needles, the skin tissue which has entered the through hole cannot be easily expelled only by a flow of the liquid drug.

An object of the present invention is to provide a microneedle that improves smooth administration of a liquid drug through a through hole.

Solution to Problem

In order to attempt to improve or even solve the above problem, a microneedle includes a base having a support surface; and a projection that protrudes from the support surface, the projection having a through hole that penetrates the projection in an extending direction of the projection, wherein the projection includes a flow path expansion section which is configured to expand a communication path that communicates between an inner space of the through hole and a space surrounding the projection in response to an increase in pressure of a fluid flowing in the through hole.

According to the above configuration, when a pressure of a fluid flowing in the through hole increases due to clogging of the through hole by skin tissue, the communication path expands and thus the flow path of a fluid in the projection expands. This allows the skin tissue in the through hole to move, which better facilitates declogging of the through hole. As a result, smoother administration of a liquid drug through a through hole can be performed.

In the above configuration, the communication path is preferably closed when a fluid does not flow in the through hole.

According to the above configuration, leakage of liquid drug to a site other than the intended site for administration of the liquid drug can be reduced compared with a configuration in which the communication path is normally open.

In the above configuration, a peripheral surface of the projection preferably includes lateral faces extending from the support surface and a top face connected to the lateral faces, the top face is inclined relative to the support surface, the through hole is preferably open at the top face, and a tip of the projection is preferably located on an edge of the top face as viewed in a direction perpendicular to the support surface.

According to the above configuration, the projection is readily pierced into the skin and skin tissue is prevented from entering the through hole, compared with a configuration in which the projection has a cone or pyramid shape which tapers toward the center through hole.

In the above configuration, assuming that the top face is divided into a region close to the tip of the projection and a region farther from the tip of the projection as viewed in a direction perpendicular to the support surface, the communication path is preferably located in the region farther from the tip.

In a configuration in which the tip of the projection is located on the edge of the top face, the portion of the projection closer to the tip will undergo a larger force applied by the skin when the projection is pierced into the skin. Accordingly, in the configuration having the communication path disposed in a region farther from the tip of the projection, that is, a region which is less likely to have a force applied thereon in piercing the skin, a decrease in strength of the projection can be reduced.

In the above configuration, the through hole preferably has an open end that is open at a distal end of the projection, and the flow path expansion section is preferably a linear portion that extends from the through hole to the peripheral surface of the projection, as well as extending from an open end of the through hole toward the support surface as viewed in a direction parallel with the support surface, and is preferably configured to expand a cut formed at a position of the flow path expansion section as the communication path in response to an increase in pressure of the fluid flowing in the through hole.

According to the above configuration, the flow path expansion section is preferably implemented. In addition, the communication path expands wider as it is closer to the distal end of the projection, and the degree of expansion of the flow path in which the liquid drug flows is smaller as it is closer to the proximal end of the projection. Accordingly, when the communication path is open, the liquid drug supplied to the projection is better prevented from flowing out from the projection at a position near the support surface. Therefore, leakage of the liquid drug onto the skin surface can be better prevented.

In the above configuration, an end of the flow path expansion section is preferably spaced from the support surface as viewed in a direction parallel with the support surface.

According to the above configuration, when the communication path is open, the liquid drug supplied to the projection is more reliably prevented from flowing out from the projection at a position near the support surface. Therefore, leakage of the liquid drug onto the skin surface can be more reliably prevented.

In the above configuration, a pressure of the fluid when the flow path expansion section starts to expand the communication path is preferably 0.20 MPa or less.

According to the above configuration, since the communication path expands before the pressure of the liquid drug flowing in the through hole exceeds 0.20 MPa, a force required to apply pressure to the liquid drug in administration of the liquid drug can be reduced.

In the above configuration, an area of an opening formed by the through hole on the peripheral surface of the projection when a fluid does not flow in the through hole is preferably in a range of $5.0 \times 10^{-4}$ mm$^2$ or more and $2.0 \times 10^{-1}$ mm$^2$ or less.

In a configuration in which the opening, which is an outlet port for the liquid drug, has a micro size within the above range, the through hole is more susceptible to clogging by skin tissue. When such a microneedle is configured to have the flow path expansion section, a liquid drug can be more smoothly delivered through a micro-sized through hole, which is more highly advantageous.

Advantageous Effects of Invention

According to the present invention, smoother administration of a liquid drug via a through hole of the microneedle is desired.

BRIEF DESCRIPTION OF THE DRAWINGS

FIGS. 7A and 7B are views of a microneedle of an embodiment, in which FIG. 7A shows a projection when a communication path is closed, and FIG. 7B shows a projection when a communication path is open.

DETAILED DESCRIPTION

Description of Representative Embodiments

It will be understood that the following description relates to representative embodiments of the present invention. The present invention is not intended to be limited to the following representative embodiments and modified examples.

With reference to FIGS. 1 to 6, 7A, and 7B, an embodiment of a microneedle will be described.

[Overall Configuration of Microneedle]

Figure 1:
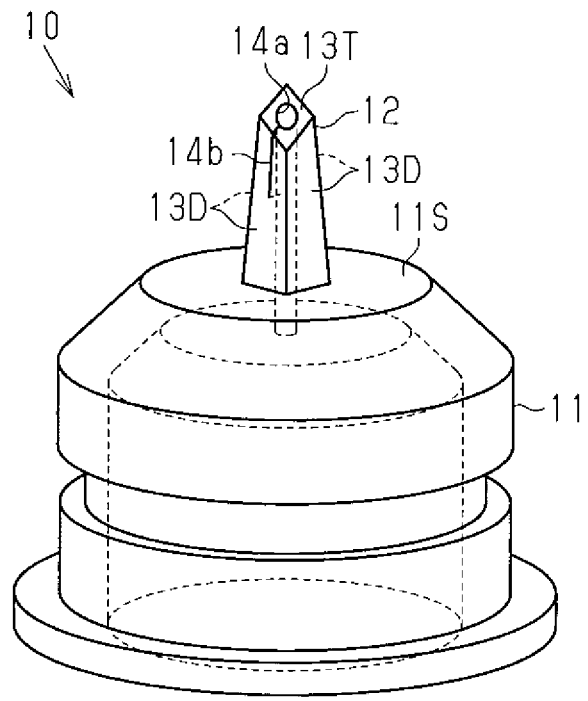
FIG. 1 is a perspective view which illustrates a perspective structure of a microneedle according to an embodiment.

As shown in FIG. 1, a microneedle 10 includes a base 11 in a tubular shape and a projection 12 protrudes from the base 11.

The base 11 has a hollow shape. The base 11 has a support surface 11S on an end face of one of both ends of the tubular shape, and an opening on the other end, which is opposite to the support surface 11S. The support surface 11S supports a proximal end of the projection 12. The shape of the support surface 11S is not limited, and may be a circular or polygonal shape.

The base 11 may have a cylindrical shape or a prism shape extending from the end on which the support surface 11S is located to the end opposite to the support surface 11S. Further, the base 11 may have a portion in which the outer diameter varies gradually or in a stepwise manner between both ends of the tubular shape. For example, as shown in FIG. 1, the base 11 may have a portion in which the outer diameter gradually decreases toward the support surface 11S or a portion having a reduced outer diameter.

The projection 12 protrudes from the support surface 11S and extends in the direction opposite to the extending direction of the base 11 with respect to the support surface 11S. The projection 12 has a truncated quadrangular pyramid shape with the truncated surface being inclined relative to the extending direction of the projection 12. The projection 12 has four lateral faces 13D extending from a rectangular bottom face, which is defined on the support surface 11S, and a top face 13T, which is inclined relative to the bottom face. That is, the peripheral surface of the projection 12 is composed of four lateral faces 13D and one top face 13T connected to these lateral faces 13D. The edges of the top face 13T are all inclined relative to the support surface 11S, and among the edges from the support surface 11S of the projection 12 to the vertices of the top face 13T, the edge to the rearmost vertex in the drawing sheet has the largest length.

The projection 12 has a through hole 14a that penetrates the projection 12 in the extending direction of the projection 12 such that the inner space of the through hole 14a communicates with the inner space of the base 11. When viewed in a direction perpendicular to the support surface 11S, the through hole 14a is open at the center of the top face 13T. That is, the through hole 14a has an open end which is open to the distal end of the projection 12. In administration of a liquid drug, the liquid drug supplied into the inner space of the base 11 flows through the through hole 14a, and exits the microneedle 10 via an opening at the top face 13T.

The through hole 14a may be formed to penetrate through the base 11 to thereby communicate with the inner space of the base 11. Alternatively, the inner diameter of the base 11 may be formed to gradually decrease toward the through hole 14a so that the inner space of the through hole 14a communicates with the inner space of the base 11.

The projection 12 has a flow path expansion section 14b configured to communicate between the inner space of the through hole 14a and the space surrounding the projection 12. The flow path expansion section 14b extends from the open end of the through hole 14a toward the support surface 11S along the through hole 14a. More specifically, the flow path expansion section 14b is a cut formed in the projection 12 to extend from the through hole 14a to one of the lateral faces 13D of the projection 12, as well as extending from the top face 13T of the projection 12 toward the support surface 11S.

This cut is not limited to those formed by cutting the projection 12, and may be formed as a tear in the projection 12. Alternatively, the cut may be formed by supplying flows of the material of the projection 12 so that they meet each other but do not become integrated with each other. The projection 12 may be produced to have such a portion, which is formed by supplying the flows of the material so that they meet each other without being integrated with each other, in the flow path expansion section 14b.

As the flow path expansion section 14b opens, a communication path that communicates between the inner space of the through hole 14a and the space surrounding the projection 12 is provided. In other words, when the flow path expansion section 14b is open, the above communication path is open so that the inner space of the through hole 14a communicates with the space surrounding the projection 12. On the other hand, when the flow path expansion section 14b is closed, the above communication path is closed to thereby separate the inner space of the through hole 14a from the space surrounding the projection 12.

When a liquid drug, that is, a fluid, does not flow in the through hole 14a, the flow path expansion section 14b is closed. When a fluid flows in the through hole 14a and the pressure of the fluid becomes a predetermined pressure or more, the flow path expansion section 14b opens. In other words, the flow path expansion section 14b is configured to increase the width of the communication path in response to an increase in pressure of the fluid flowing in the through hole 14a. The pressure of the fluid flowing in the through hole 14a when the flow path expansion section 14b starts to open is preferably in the range of 0.05 MPa or more and 0.20 MPa or less.

In administration of a liquid drug using the microneedle 10 assembled to a 1 mL syringe, a pressure typically required to push a piston when a liquid drug more smoothly flows in the through hole 14a is in the range of approximately from 0.01 MPa to 0.04 MPa. Accordingly, in the configuration that allows the flow path expansion section 14b to open when a liquid drug is pressed at a pressure higher than this pressure, the communication path is appropriately expanded when the flow of the liquid drug is blocked. In addition, it is a burden for a user to administer a liquid drug while pushing a piston by hand at a pressure higher than 0.20 MPa. Accordingly, the flow path expansion section 14b preferably starts to open before the pressing force reaches this pressure, that is, when the liquid drug is pressed at a pressure of 0.20 MPa or less.

The microneedle 10 may include a single projection 12 or a plurality of projections 12. When the microneedle 10 includes a single projection 12, the projection 12 is preferably located at a center of the support surface 11S. In a configuration in which the support surface 11S has a symmetric shape and the projection 12 protrudes from the center of the support surface 11S, the support surface 11S easily stays in a horizontal position when the projection 12 is pierced into the skin. Further, when the microneedle 10 includes a plurality of projections 12, the plurality of projections 12 are arranged, for example, in a grid, circular, or coaxial pattern on the support surface 11S.

[Detailed Configuration of Projections]

Figure 2:
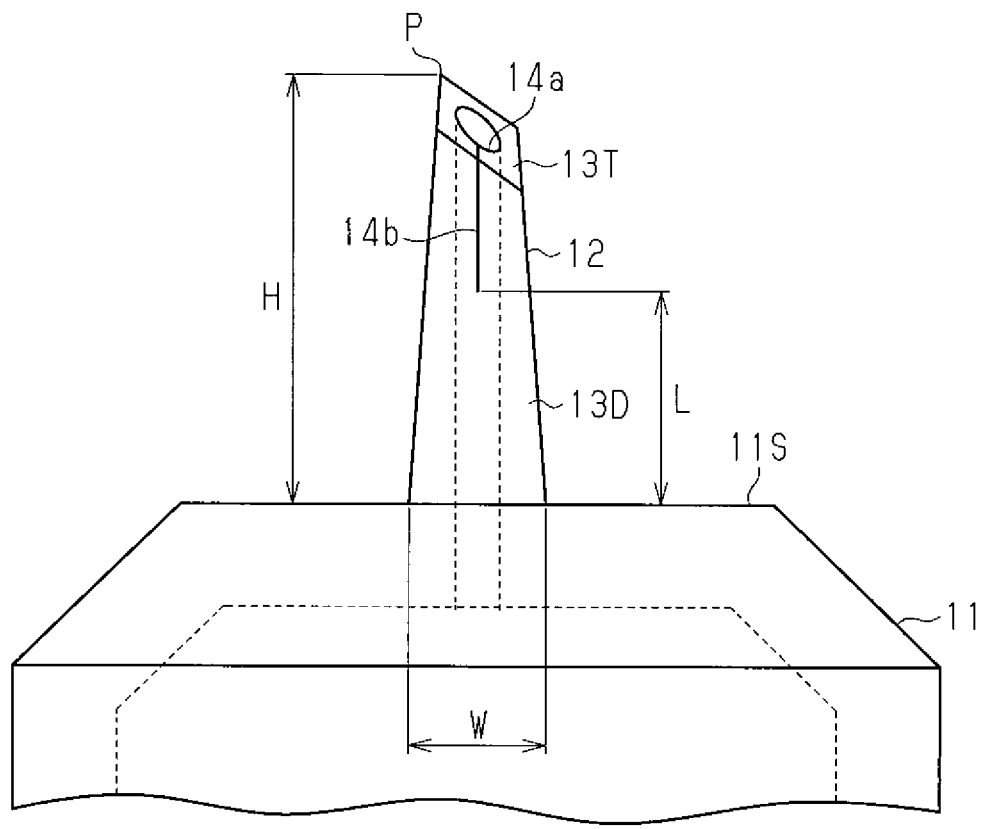
FIG. 2 is a side view which illustrates a side structure of a projection of a microneedle according to an embodiment.
Figure 3:
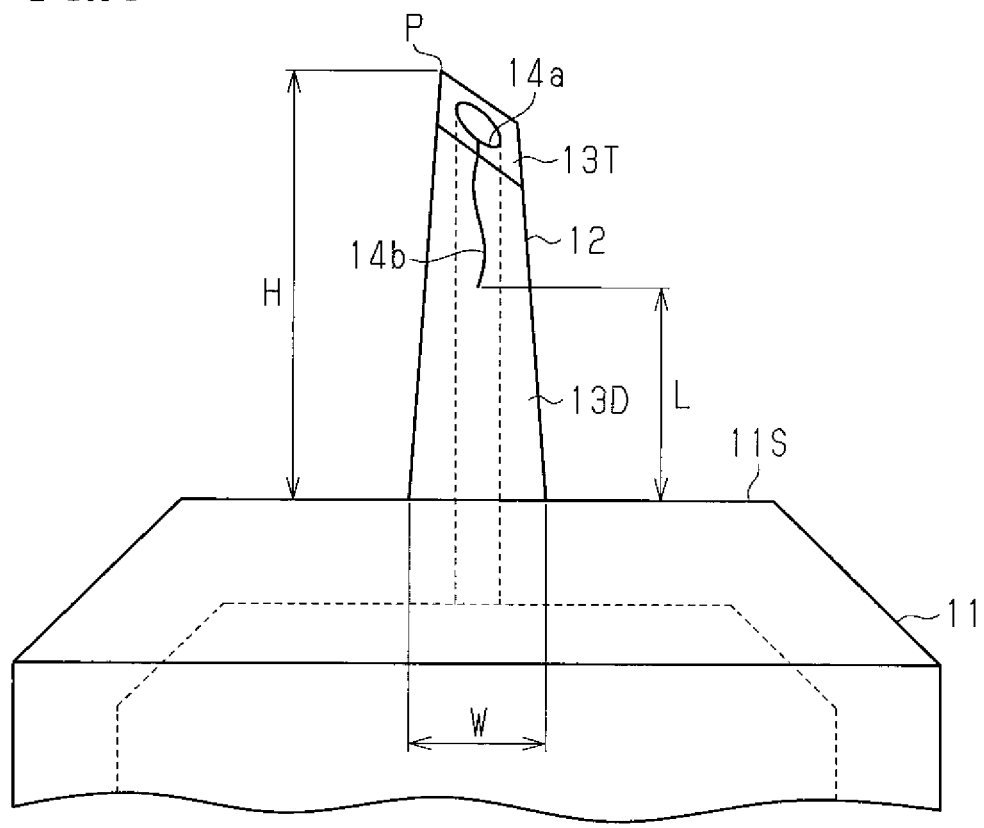
FIG. 3 is a side view which illustrates a side structure of a projection of a microneedle according to a modified example.
Figure 4:
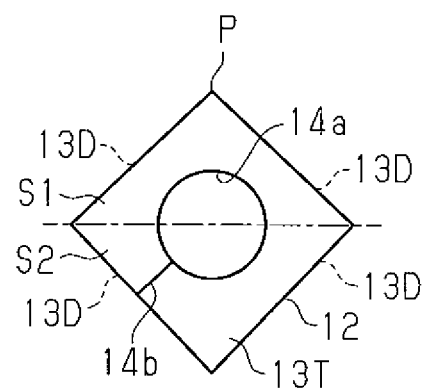
FIG. 4 is a top view of a projection of a microneedle according to an embodiment as viewed in a direction perpendicular to a support surface of a base.

With reference to FIGS. 2 to 4, a detailed configuration of the projection 12 will be described.

As shown in FIG. 2, a tip P of the projection 12 is located on an edge of the top face 13T when the side surface 13D of the projection 12 on which the flow path expansion section 14b is provided is viewed in a direction parallel with the support surface 11S.

A length H of the projection 12 is a length from the support surface 11S to the tip of the projection 12 in a direction facing the support surface 11S, that is, a direction perpendicular to the support surface 11S. The length H of the projection 12 is preferably a length that penetrates the stratum corneum, which is the outermost layer of the skin, and does not reach the nerve cells, and is specifically in the range of 200 μm or more and 2000 μm or less.

When the side surface 13D of the projection 12 is viewed in a direction in which the support surface 11S extends, that is, in a direction parallel with the support surface 11S, a width W of the projection 12 is a length of a portion sandwiched between two edges extending from the support surface 11S in the direction parallel with the support surface 11S. The width W of the projection 12 gradually decreases from the proximal end toward the distal end of the projection 12. The minimum value and the maximum value of the width W of the projection 12 is preferably in the range of 20 μm or more and 1000 μm or less.

When the flow path expansion section 14b is closed, an area of the opening formed by the through hole 14a on the peripheral surface of the projection 12, that is, an area of the opening defined by the top face 13T is preferably in the range of $5.0 \times 10^{-4}$ mm$^2$ or more and $2.0 \times 10^{-1}$ mm$^2$ or less. Further, an area of the above opening when the flow path expansion section 14b is closed is more preferably in the range of $5.0 \times 10^{-4}$ mm$^2$ or more and $1.0 \times 10^{-2}$ mm$^2$ or less. Even if the area of the opening is small, a liquid drug can be more smoothly delivered through the through hole 14a as the flow path expansion section 14b opens.

The flow path expansion section 14b extends from the top face 13T of the projection 12 toward the support surface 11S and preferably does not reach the support surface 11S when the side surface 13D on which the flow path expansion section 14b is provided is viewed in a direction parallel with the support surface 11S. That is, an end of the flow path expansion section 14b is preferably spaced from the support surface 11S. Specifically, when the side surface 13D on which the flow path expansion section 14b is provided is viewed in a direction parallel with the support surface 11S, a length between the support surface 11S and one of the ends of the flow path expansion section 14b which is closer to the support surface 11S in a direction perpendicular to the support surface 11S is referred to as an end distance L. The end distance L is preferably one-fifth or more of the length H of the projection 12, and more preferably one-third or more of the length H of the projection 12.

Since the end of the flow path expansion section 14b is spaced from the support surface 11S, a liquid drug supplied to the projection 12 is prevented from leaking from a position adjacent to the support surface 11S of the projection 12, that is, adjacent to the skin while the flow path expansion section 14b is open. Accordingly, the liquid drug intended to be administered into the skin can be better prevented from leaking onto the skin. These effect can be more favorably obtained when the end distance L is one-fifth or more of the length H of the projection 12. Further, these effect can be further enhanced when the end distance L is one-third or more of the length H of the projection 12.

Moreover, the projection 12 has a higher strength in a configuration in which the end of the flow path expansion section 14b is spaced from the support surface 11S compared with a configuration in which the end of the flow path expansion section 14b reaches the support surface 11S.

When the side surface 13D on which the flow path expansion section 14b is provided is viewed in a direction parallel with the support surface 11S, the flow path expansion section 14b may extend in a straight shape in a direction perpendicular to the support surface 11S or may extend in a straight shape inclined relative to a direction perpendicular to the support surface 11S as far as it extends from the top face 13T of the projection 12 toward the support surface 11S. Alternatively, when the side surface 13D on which the flow path expansion section 14b is provided is viewed in a direction parallel with the support surface 11S, the flow path expansion section 14b may extend in a curved shape. The configuration having the flow path expansion section 14b extending in a curved shape is shown in FIG. 3.

In a configuration in which the flow path expansion section 14b extends in a curved shape, the projection 12 may have an increased contact area in the flow path expansion section 14b compared with a configuration in which the flow path expansion section 14b extends in a straight shape. Further, the above area can be finely adjusted by varying the form of the curved shape. Accordingly, a pressure of the fluid flowing in the through hole 14a when the flow path expansion section 14b starts to open can be finely set from a wide range of values, which increases the degree of freedom for the pressure setting.

Further, in a configuration in which the flow path expansion section 14b extends in a curved shape, the flow path expansion section 14b is not opened compared with a configuration in which the flow path expansion section 14b extends in a straight shape in the case except for when a pressure of the fluid flowing in the through hole 14a increases, that is, a force other than that expands the through hole 14a acts on the flow path expansion section 14b.

FIG. 4 illustrates the top face 13T of the projection 12 as viewed in a direction perpendicular to the support surface 11S of the base 11.

The tip P of the projection 12 is located on the edge of the top face 13T, and the through hole 14a is located at the center of the top face 13T as viewed in a direction perpendicular to the support surface 11S. Further, the flow path expansion section 14b extends from the through hole 14a to one of the side surfaces 13D. This configuration is the same when the projection 12 is viewed in a direction perpendicular to the top face 13T.

When the top face 13T as viewed in a direction perpendicular to the support surface 11S is divided into two regions by a straight line connecting two opposite vertices on the top face 13T, i.e., a region S1 close to the tip P and a region S2 farther from the tip P, the flow path expansion section 14b is preferably included in the region S2 farther from the tip P. That is, when four side surfaces 13D of the projection 12 are divided into two side surfaces 13D close to the tip P and the two side surfaces 13D farther from the tip P, the flow path expansion section 14b is preferably disposed on the side surface 13D which is farther from tip P. In other words, the side surface 13D having the flow path expansion section 14b is preferably a side surface 13D which does not include the tip P, such that the side surface 13D having the flow path expansion section 14b and the top face 13T share one of the edges of the top face 13T which is located on the lower side of the slope, that is, the edge closer to the proximal end of the projection 12.

Further, the region S1 and the region S2 may be the regions divided by the perpendicular bisector to the line segment joining the tip P and the edge of the top face 13T through the center of gravity of the top face 13T. In this case as well, the flow path expansion section 14b is preferably included in the region S2, which is farther from the tip P.

With the configuration in which the projection 12 has the slant top face 13T and the tip P is located on the edge of the top face 13T, the projection 12 is pierced into the skin in administration of liquid drug by the tip P which is spaced from the through hole 14a. On the other hand, with the configuration in which the projection has a cone or pyramid shape which tapers toward the center through hole, the projection does not have a sharp tip. In administration of liquid drug, the portion of the projection 12 around the through hole is first pierced into the skin. As a consequence, the former configuration, that is, the configuration of the present embodiment, facilitates piercing of the projection 12 into the skin and prevents skin tissue from entering into the through hole 14a compared with the latter configuration.

On the other hand, in a configuration in which the tip P is located on the edge of the top face 13T, the portion of the projection 12 closer to the tip P will undergo a larger force applied by the skin when the projection 12 is pierced into the skin. Therefore, in a configuration in which the flow path expansion section 14b is disposed in the portion of the projection 12 farther from the tip P, that is, the portion which is less likely to have a force applied thereon in piercing the skin, a decrease in strength of the projection 12 in piercing the skin can be reduced among the configurations having a cut as the flow path expansion section 14b.

Further, the flow path expansion section 14b may be disposed at the interface between the two side surfaces 13D, that is, on the edge shared by the two side surfaces 13D. However, the flow path expansion section 14b can be fabricated more easily in a configuration in which the flow path expansion section 14b is disposed in one of the side surfaces 13D, since the distance from the through hole 14a to the peripheral surface of the projection 12 at the position where the flow path expansion section 14b is formed is smaller.

[Method for Producing Microneedle]

Materials and production methods for the microneedle 10 will be described.

The projection 12 can be made of any material as long as the material can form the projection 12 having the rigidity to such an extent that the flow path expansion section 14b is opened in response to an increase in pressure of the fluid flowing in the through hole 14a.

For example, the projection 12 may be made of metal materials such as silicon, stainless steel, titanium, cobalt-chromium alloy, magnesium alloy, and the like. Further, the projection 12 may be made of resin materials such as commodity plastics, medical grade plastics, and plastics for cosmetic product. Examples of the resin material include polyethylene, polypropylene, polystyrene, polyamide, polycarbonate, cyclic polyolefin, polylactic acid, polyglycolic acid, polycaprolactone, acrylic, urethane resin, aromatic polyether ketone, epoxy resin, and copolymer materials of these resins.

Materials for the base 11 are not specifically limited, and the base 11 may be made of, for example, a material described above as the material for the projection 12.

The microneedle 10 may be formed as a unitary molded product having the base 11 and the projection 12 integrally formed, or a combination of the base 11 and the projection 12 which are joined to each other after they are separately formed, or a combination of a metal material and a resin material. For example, the projection 12 may be made of a metal and the base 11 may be made of a resin, or vice versa.

When the base 11 and the projection 12 are separately formed, or when the microneedle 10 is formed of a combination of a metal material and a resin material, the separate components of the microneedle 10 can be closely joined by using a sealing agent, adhesive, gasket, O-ring, and the like, and a combination thereof as necessary.

Examples of the production method for the microneedle 10 include machining the outer shape of the base 11 and the projection 12, followed by forming the through hole 14a and the flow path expansion section 14b. Alternatively, the base 11 and the projection 12 may be formed by injection molding when the microneedle 10 is made of a resin material. When injection molding is used, the flow path expansion section 14b may be formed by filling a resin in two circumferential directions toward a position where the flow path expansion section 14b is intended to be formed so that two flows of resin meet at the position in a state that the surface of the resin is cured. Alternatively, the flow path expansion section 14b may be formed by machining or the like, which is performed as a post-process of injection molding. Further, when the microneedle 10 is made of two different materials, the microneedle 10 may be formed by insert molding, double-molding, or the like. Examples of processing method for forming the flow path expansion section 14b after the outer shape of the base 11 and the projection 12 is formed include laser processing, ultrasonic processing, and the like.

Figure 5:
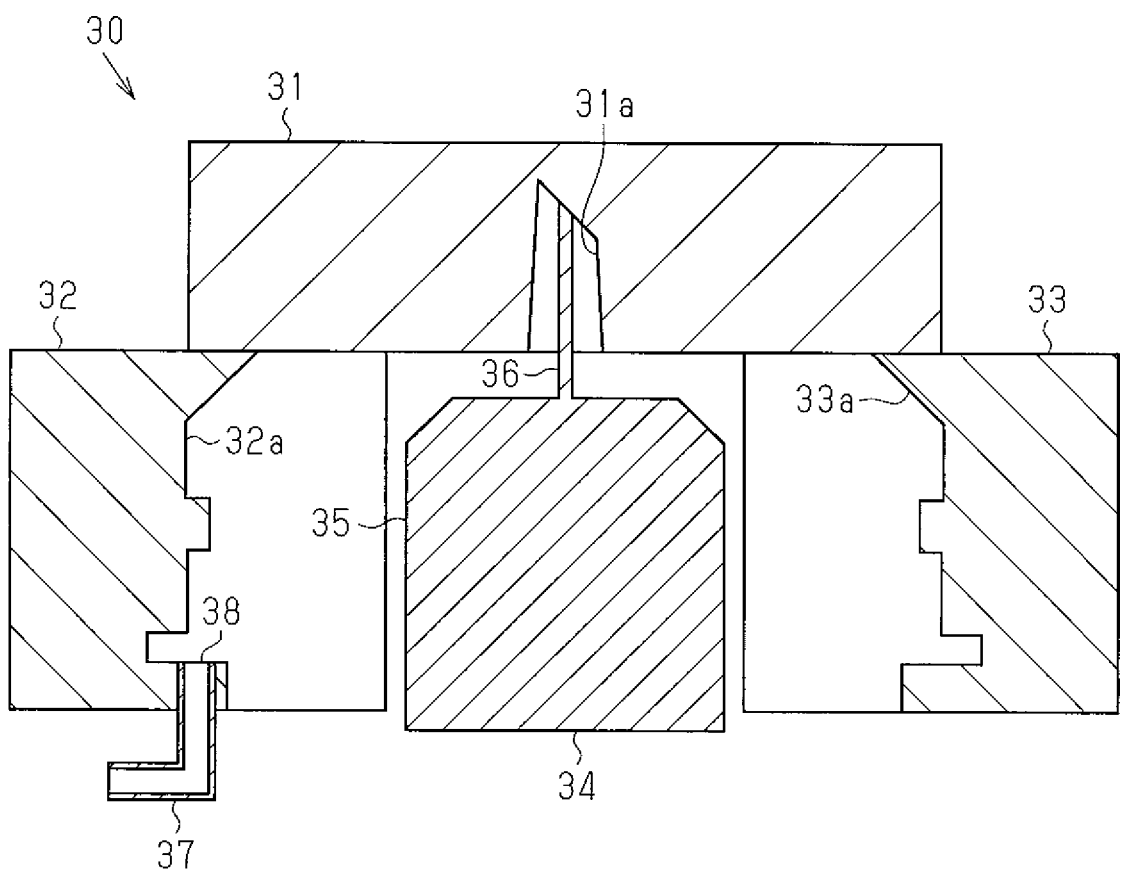
FIG. 5 is a schematic view for illustrating a production method of a microneedle according to an embodiment.

With reference to FIG. 5, the method for producing the microneedle 10 by integral molding using injection molding will be described as an example of the production method for the microneedle 10.

As shown in FIG. 5, a mold 30 for use in injection molding includes a fixed mold 31, a first movable mold 32, a second movable mold 33, and a core pin 34. The fixed mold 31 has a projection forming groove 31a having a shape corresponding to the shape of the projection 12. A portion of the fixed mold 31 in which the projection forming groove 31a is formed can be replaceable so that the shape of the projection forming groove 31a in the fixed mold 31 can be modified.

The first movable mold 32 and the second movable mold 33 are molds which are movable relative to the fixed mold 31. The first movable mold 32 has a first molding groove 32a corresponding to the shape of one of the halves of the base 11 located under the tip P of the projection 12, while the second movable mold 33 has a second molding groove 33a corresponding to the other of the halves of the base 11.

The core pin 34 includes a main body 35 and a distal portion 36. The main body 35 is a portion of the microneedle 10 which forms an inner peripheral surface of the base 11, and the distal portion 36 is a portion which forms the through hole 14a of the projection 12.

A runner 37 for introducing a resin into the mold 30 is disposed on the first movable mold 32. A portion of the first molding groove 32a to which the runner 37 is connected is a gate 38.

In fabrication of the microneedle 10, a molten resin is introduced into the mold 30 from an injection molding machine. Accordingly, a resin flows into the first molding groove 32a through the runner 37 and the gate 38, and then into the projection forming groove 31a and the second molding groove 33a.

Here, a flow speed of the resin introduced through the gate 38, a flow speed of the resin flowing in the mold 30, the positions and number of the gates 38, a timing when the resin is introduced through the gate 38, or the like can be adjusted so that the flows of resin, which flow in two circumferential directions toward the position where the flow path expansion section 14b is intended to be formed in the projection forming groove 31a, meet at the position in a state that the surface of the resin is cured.

For example, the mold 30 when in use is mounted in a mold base having a flow path for compressed air for cooling so that compressed air is supplied into the flow path during filling of the mold 30 with resin so as to partially cool the mold 30. A flow rate of the compressed air can be adjusted so that the mold 30 has a temperature gradient to thereby adjust the flow speed of the resin flowing in the projection forming groove 31a.

Thus, an interface is formed between the flows of resin when they meet each other in the projection forming groove 31a. This interface provides the flow path expansion section 14b.

After the resin introduced into the mold 30 is fully cured, the first movable mold 32, the second movable mold 33, and the core pin 34 are displaced to take out the microneedle 10 from the mold 30.

[Effects]

Figure 6:
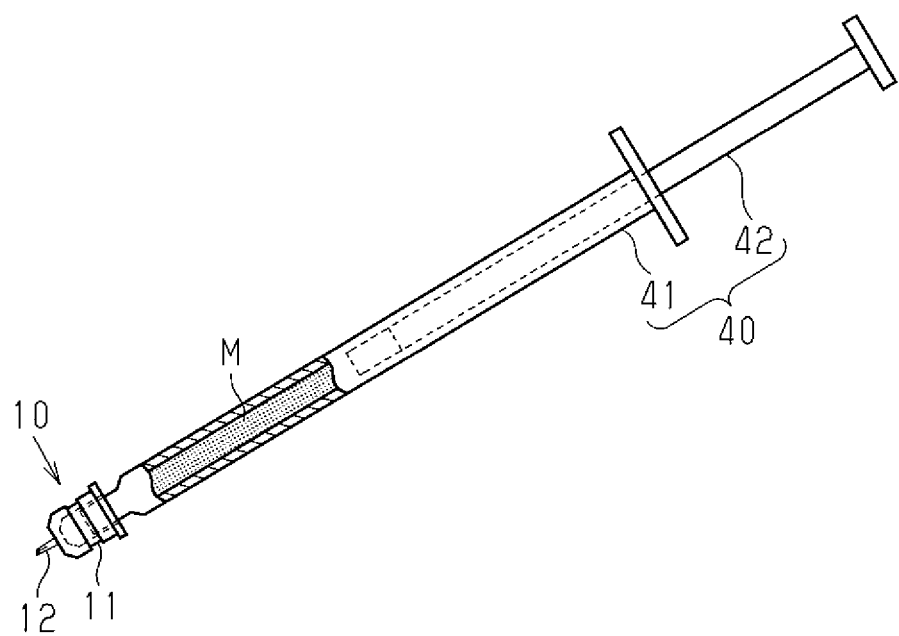
FIG. 6 is a view of a syringe barrel in which a microneedle of an embodiment is attached, which is illustrated with part of an outer cylinder of the syringe barrel removed.

With reference to FIGS. 6 and 7, a structure of a microneedle 10 will be described.

As shown in FIG. 6, the microneedle 10 is mounted on an end of the outer cylinder 41 of the syringe barrel 40. In administration of a liquid drug, the microneedle 10 is pressed against the skin of target for administration of the liquid drug to thereby pierce the skin using the projection 12. Then, while the projection 12 is pierced into the skin, the plunger 42 is pushed into the microneedle 10. As the plunger 42 is pushed into the microneedle 10, a liquid drug M in the outer cylinder 41 is supplied into the base 11 of the microneedle 10, and then into the through hole 14a of the projection 12. Then, the liquid drug M flows out from the opening on the top face 13T on the projection 12 and flows into the skin.

Figure 7A:
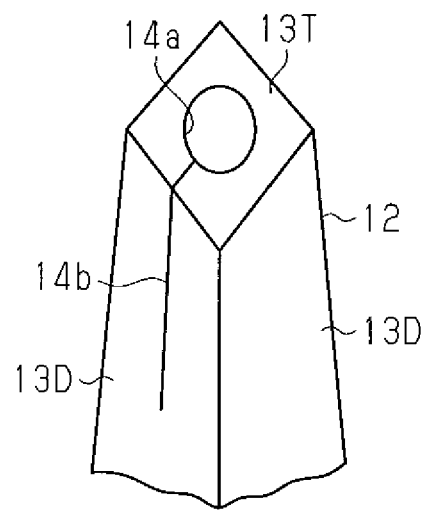
Figure 7B:
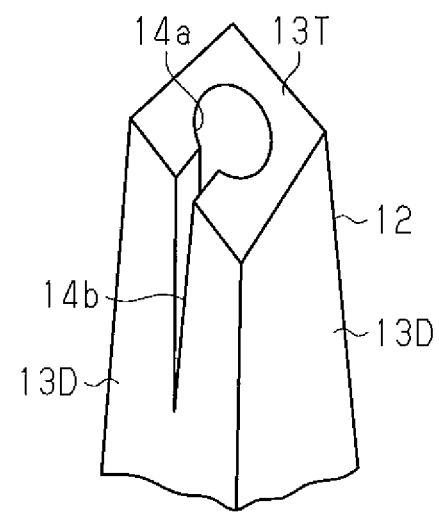

As shown in FIG. 7A, when a liquid drug does not flow in the through hole 14a and when a pressure of the liquid drug flowing in the through hole 14a is small, the flow path expansion section 14b is closed. That is, a communication path that communicates between the inner space of the through hole 14a and the space surrounding the projection 12 is closed. When skin tissue enters the through hole 14a, it clogs part of the through hole 14a. As a pressure of the liquid drug flowing in the through hole 14a increases, a force attempting to expand the through hole 14a increases. As a result, the flow path expansion section 14b opens as shown in FIG. 7B. That is, the projection 12 is separated at a position from the top face 13T to the side surface 13D of the projection 12 into two parts, forming a gap which communicates with the through hole 14a. Thus, the above-mentioned communication path is open, expanding the flow path for the liquid drug in the projection 12. The communication path opens to the top face 13T of the projection 12 and the side surface 13D.

As a result, skin tissue in the through hole 14a is expelled from the through hole 14a to thereby remove clogging of the through hole 14a, allowing for smoother administration of the liquid drug. Moreover, an injection pressure of the liquid drug is kept at a low pressure compared with the case in which administration of liquid drug continues while the through hole 14a is still clogged. Accordingly, leakage of the liquid drug onto the skin surface due to reaction force from inside the skin can also be prevented.

Further, when the pressure of liquid drug flowing in the through hole 14a increases due to not only clogging of the through hole 14a but also high pressure in the skin or the like, the flow path for a liquid drug is expanded as the flow path expansion section 14b opens. As a result, an injection pressure of the liquid drug is kept at low pressure, which also prevents leakage of the liquid drug onto the skin surface.

In a configuration in which the flow path expansion section 14b is a cut extending from the top face 13T to the side surface 13D of the projection 12, that is, a cut formed at a position of the flow path expansion section 14b is opened as a communication path, the communication path expands wider as it is closer to the top face 13T. That is, the closer to the proximal end of the projection 12, the smaller the extent of expansion of the flow path for the liquid drug. Accordingly, when the flow path expansion section 14b is open, the liquid drug supplied to the projection 12 is prevented from flowing out from the projection 12 at a position near the support surface 11S. Therefore, leakage of the liquid drug onto the skin surface can be prevented.

In addition to providing the flow path expansion section 14b, as a technique of reducing clogging of the through hole 14a for smoother administration of a liquid drug, an increase in diameter of the through hole 14a is possible. However, increasing the diameter of the through hole 14a involves an increase in the entire dimensions of the projection 12 in order to ensure the strength of the projection 12. The large sized projection 12 causes a problem of increase in resistance in piercing the projection 12 into the skin. Further, the larger the diameter of the through hole 14a, the larger the outlet port for a liquid drug. Accordingly, there is always a risk of leakage of liquid drug to a site other than the intended site for administration of the liquid drug, for example, into the skin or onto the skin surface, during administration of the liquid drug. According to the microneedle 10 of the present embodiment, smoother administration of the liquid drug is possible while preventing the above problems.

When the flow path expansion section 14b is open, a risk of leakage of liquid drug to a site other than the intended site for administration of the liquid drug increases compared with the case when the flow path expansion section 14b is closed. However, according to the microneedle of the present embodiment, a risk of leakage of liquid drug can be minimized since the flow path expansion section 14b is closed until the pressure of liquid drug flowing in the through hole 14a becomes higher. Further, when the through hole 14a does not have clogging or the like and the pressure of liquid drug flowing in the through hole 14a remains low, the risk of leakage of liquid drug can remain low during administration of the liquid drug.

In addition, after the clogging of the through hole 14a is cleared, the flow path expansion section 14b may be closed as in the initial state, or may remain open.

As described above, according to the microneedle unit 10 of the present embodiment, advantageous effects listed below can be achieved.

(1) The flow path expansion section 14b which is configured to expand a communication path that communicates between an inner space of the through hole 14a and a space surrounding the projection 12 in response to an increase in pressure of a fluid flowing in the through hole 14a is formed in the projection 12. With this configuration, the communication path expands when skin tissue enters the through hole 14a and the pressure of a fluid flowing in the through hole 14a increases, thereby expanding a flow path for a fluid in the projection 12. This allows skin tissue in the through hole 14a to move, which better facilitates declogging of the through hole 14a. As a result, more smoother administration of a liquid drug through a through hole 14a can be performed.

(2) The above communication path is closed when a fluid does not flow in the through hole 14a. Accordingly, a risk of leakage of liquid drug to a site other than the intended site for administration of the liquid drug can be reduced compared with a configuration in which the communication path is normally open. Further, since an absent portion of the structure of the projection 12 can be small compared with a configuration, in which the communication path is normally open, the entire dimensions of the projection 12 necessary for ensuring the strength of the projection 12 can be small and thin. Accordingly, since an increase in resistance in piercing the projection 12 into the skin can be reduced, the projection 12 has an advantageous structure in piercing the skin in a reliable manner.

(3) The peripheral surface of the projection 12 is composed of the side surface 13D extending from the support surface 11S, the top face 13T inclined relative to the support surface 11S, the through hole 14a open at the top face 13T, and the tip P of the projection 12 located on the edge of the top face 13T as viewed in a direction perpendicular to the support surface 11S. With this configuration, the projection 12 is readily pierced into the skin and skin tissue is prevented from entering the through hole 14a, compared with a configuration in which the projection has a cone or pyramid shape which tapers toward the center through hole.

(4) In a configuration in which the flow path expansion section 14b is included in a region of the top face 13T which is farther from the tip P of the projection 12, the flow path expansion section 14b is disposed in a region of the projection 12 which is less likely to have a force applied thereon in piercing the skin. Accordingly, among the configurations having a communication path composed of the flow path expansion section 14b formed in the projection 12, a decrease in strength of the projection 12 in piercing the skin can be reduced.

(5) The flow path expansion section 14b is a cut extending from the through hole 14a to one of the lateral faces 13D of the projection 12, as well as extending from the top face 13T of the projection 12 toward the support surface 11S, that is a cut formed to extend from the top face 13T of the projection 12 and along the side surface 13D. The flow path expansion section 14b expands the above cut as a communication path. With this configuration, the flow path expansion section 14b expands wider as it is closer to the top face 13T, and the degree of expansion of the flow path in which the liquid drug flows is smaller as it is closer to the proximal end of the projection 12. Accordingly, when the flow path expansion section 14b is open, the liquid drug supplied to the projection 12 is prevented from leaking out onto the skin surface.

(6) The end of the flow path expansion section 14b is spaced from the support surface 11S as viewed in a direction parallel with the support surface 11S. With this configuration, when the flow path expansion section 14b is open, the liquid drug supplied to the projection 12 is more reliably prevented from leaking out onto the skin.

(7) In a configuration in which a pressure of a fluid flowing in the through hole 14a when the flow path expansion section 14b starts to open, that is, when the flow path expansion section 14b starts to expand the communication path, is preferably 0.20 MPa or less, a force required to press the liquid drug in administration of the liquid drug can be reduced since the communication path expands before the pressure of the liquid drug flowing in the through hole 14a exceeds 0.20 MPa.

(8) In a configuration in which an area of an opening formed by the through hole 14a on the peripheral surface of the projection 12 when a fluid does not flow in the through hole 14a is preferably in a range of $5.0 \times 10^{-4}$ mm$^2$ or more and $2.0 \times 10^{-1}$ mm$^2$ or less, the through hole 14a is susceptible to clogging by skin tissue since the opening is micro sized. When such a microneedle is configured to have the flow path expansion section 14b, a liquid drug can be more smoothly delivered through a micro-sized through hole 14a, which is highly advantageous.

The above embodiment can be implemented with modifications as described below.

Figure 8:
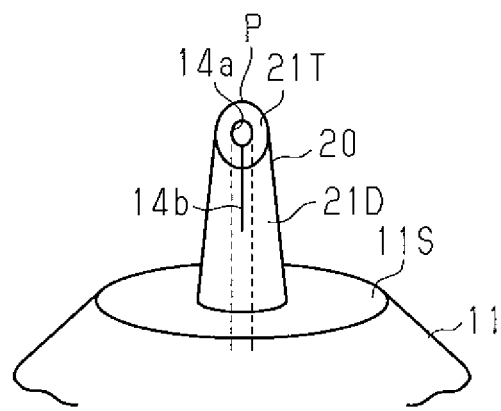
FIG. 8 is a perspective view which shows a perspective structure of a projection of a microneedle according to a modified example.

The shape of the projection 12 is not limited to those described in the above embodiment. For example, as shown in FIG. 8, a projection 20 may be truncated obliquely to the extending direction of the cone. In this case, the peripheral surface of the projection 20 is composed of a side surface 21D, which is a curved surface extending from the support surface 11S, and a top face 21T connected to the side surface 21D and inclined relative to the support surface 11S. Further, the flow path expansion section 14b is preferably formed to extend from a position on the top face 21T farthest from the tip P to the side surface 21D. In the configuration having the width W gradually increasing from the distal end to the proximal end of the projection, as with the projection truncated obliquely to the extending direction of the conical shape, the projection is prevented from decreasing in strength even if it has the flow path expansion section 14b.

Figure 9:
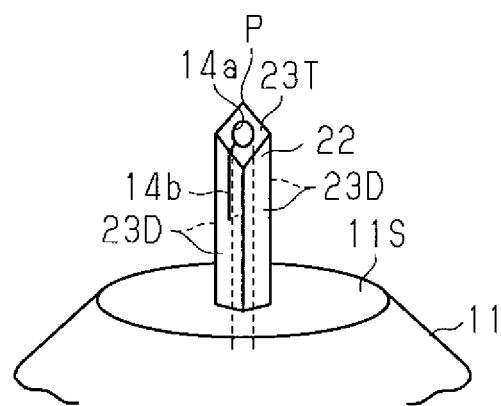
FIG. 9 is a perspective view which shows a perspective structure of a projection of a microneedle according to a modified example.

Further, the projection may have a prism shape or a cylindrical shape truncated obliquely to the extending direction thereof. FIG. 9 illustrates a projection 22 having a quadrangular prism truncated obliquely to the extending direction thereof. In this case, the peripheral surface of the projection 22 is composed of four side surfaces 23D extending from the support surface 11S and a top face 23T connected to the side surfaces 23D and inclined relative to the support surface 11S. In this case, the width W of the projection is constant from the distal end to the proximal end of the projection, and a resistance in piercing the projection into the skin can be small compared with the configuration having a varying width W.

Figure 10:
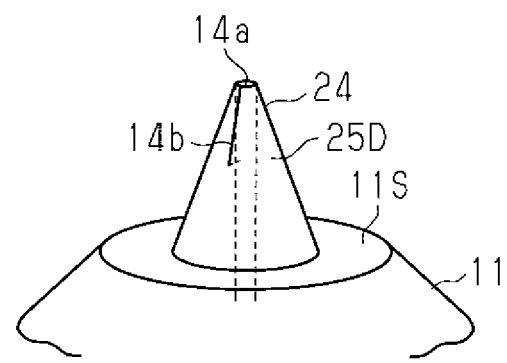
FIG. 10 is a perspective view which shows a perspective structure of a microneedle according to a modified example.

As shown in FIG. 10, the projection may not necessarily have an inclined top face, and the tip of the projection may be located at the center of the projection as viewed in a direction perpendicular to the support surface 11S. A projection 24 shown in FIG. 10 has a cone shape which tapers toward the center through hole 14a. In this case, the peripheral surface of the projection 24 is composed of a side surface 25D, which is a curved surface extending from the support surface 11S, and the tip of the projection 24 is not a sharpened vertex but an open end of the through hole 14a. In this configuration, the flow path expansion section 14b extends from the through hole 14a to the peripheral surface of the projection 24, as well as extending from an open end of the through hole 14a toward the support surface 11S as viewed in a direction parallel with the support surface 11S.

In the above configurations as well, the same effects as those described in the (1), (2), and (5) to (8) can be obtained. However, the configuration in which the peripheral surface of the projection is composed of side surfaces extending from the support surface 11S and a top face inclined relative to the support surface 11S, and the tip P of the projection is located on the edge of the top face, is preferred due to the ease of piercing the projection into the skin and prevention of skin tissue from entering the through hole 14a.

The projection is not limited to the shape illustrated in the above embodiment and FIGS. 8 to 10, and may be in any shape that can pierce the skin. For example, the projection may have two or more different shapes in the extending direction of the projection from among a pyramid, a cone, a cylinder, and a prism. Moreover, the projection may have a groove or a shoulder on the peripheral surface. Further, the top face of the projection may be curved.

The through hole 14a may be formed at a position deviated from the center of the projection 12 as viewed in a direction perpendicular to the support surface 11S. In this case as well, the flow path expansion section 14b is preferably formed at a position having a small distance from the through hole 14a to the peripheral surface of the projection 12.

The flow path expansion section 14b may not be necessarily a continuous cut as long as it is configured to expand a communication path in response to an increase in pressure of the fluid flowing in the through hole 14a.

For example, the flow path expansion section 14b may be formed by internal reforming by laser processing, ultrasonic processing, or the like, or a plurality of processed parts formed by physical change by heat, pressure, or the like. That is, the processed parts may extend from the through hole 14a to the peripheral surface of the projection 12, and may be an array of a plurality of processed parts arranged from an open end of the through hole 14a toward the support surface 11S as viewed in a direction parallel with the support surface 11S. In this case, a cut (communication path) substantially does not exist in the flow path expansion section 14b when a fluid does not flow in the through hole 14a. The projection 12 splits at the flow path expansion section 14b from a processed part having a low strength in response to an increase in pressure of a fluid flowing in the through hole 14a, thereby opening a communication path.

Further, for example, the flow path expansion section 14*b* may be a portion where flows of the material for forming the projection 12 join each other while creating an interface during fabrication, like a weld-line in resin molding, and has a lower strength than that of remaining portions. Then, the projection 12 splits at the flow path expansion section 14*b* having a low strength in response to an increase in pressure of a fluid flowing in the through hole 14*a*, thereby opening a communication path.

Thus, the flow path expansion section 14*b* may be a weakened portion having a lower strength than that of the remaining portion. In short, the flow path expansion section 14*b* may be formed as a cut before a fluid flows in the through hole 14*a* as described in the above embodiment, or alternatively, as a configuration that becomes a cut in response to an increase in pressure of a fluid flowing in the through hole 14*a* as described above. If the flow path expansion section 14*b* extends from the through hole 14*a* to the peripheral surface of the projection, as well as extending from an open end of the through hole 14*a* toward the support surface 11S as viewed in a direction parallel with the support surface 11S, and if it is configured to expand a cut as a communication path formed at a position of the flow path expansion section 14*b* in response to an increase in pressure of a fluid flowing in the through hole 14*a*, the effect of the above (5) can be obtained.

Even if the degree of expansion of the flow path expansion section 14*b* is small, formation of the communication path changes the flow of the liquid drug, which causes skin tissue in the through hole 14*a* to move and better facilitates declogging of the through hole 14*a*.

Figure 11:
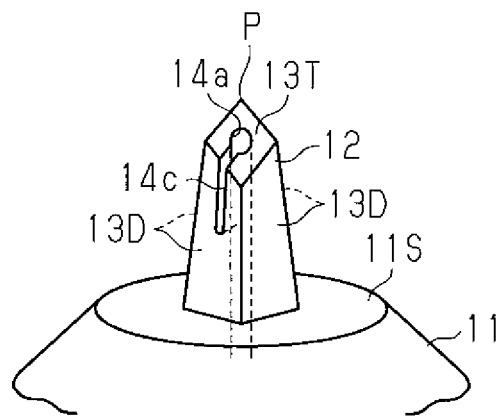
FIG. 11 is a perspective view which shows a perspective structure of a microneedle according to a modified example.

Although the flow path expansion section 14*b* in the above embodiment is closed when a fluid does not flow in the through hole 14*a*, the flow path expansion section 14*b* may be normally open. That is, the communication path may be open when a fluid does not flow in the through hole 14*a*. For example, as shown in FIG. 11, in a configuration in which the flow path expansion section 14*c* is a groove extending from the through hole 14*a* to the peripheral surface of the projection 12, as well as extending from an open end of the through hole 14*a* toward the support surface 11S as viewed in a direction parallel with the support surface 11S, and recessed toward the support surface 11S, the communication path is open when a fluid does not flow in the through hole 14*a*. Then, the flow path expansion section 14*c* further opens to expand the communication path when a pressure of a fluid flowing in the through hole 14*a* becomes a predetermined pressure or more. With this configuration as well, a similar effect to that described in the above (1) can be obtained.

In short, the flow path expansion section may have any configuration as far as it expands a communication path in response to an increase in pressure of a fluid flowing in the through hole 14*a*, regardless of whether the communication path is open or closed when a fluid does not flow in the through hole 14*a*.

However, the configuration in which communication path is closed when a fluid does not flow in the through hole 14*a* is more likely to reduce a risk of leakage of liquid drug to a site other than the intended site for administration of the liquid drug during a period before clogging occurs in the through hole 14*a*. Further, when the through hole 14*a* does not have clogging or the like and the pressure of liquid drug flowing in the through hole 14*a* remains low, a risk of leakage of liquid drug can remain low. Further, since an absent portion of the structure of the projection 12 can be small compared with a configuration in which the flow path expansion section 14*c* formed in the projection 12 is normally open as in the case of the flow path expansion section formed as a groove, the projection 12 can be prevented from decreasing in strength, and the entire dimensions of the projection 12 necessary for ensuring the strength of the projection 12 can be small.

The flow path expansion section 14*b* may be configured to open when a pressure of a fluid flowing in the through hole 14*a* becomes a predetermined pressure or more, and maintain the opening degree, or open wider as the pressure of a fluid increases.

The projection 12 may have a plurality of flow path expansion sections 14*b*. In this case, a plurality of flow path expansion sections 14*b* are preferably regularly arranged around the through hole 14*a* as viewed in a direction perpendicular to the support surface 11S.

The base 11 may not be necessarily a tubular shape if the base 11 has the support surface 11S that supports the projection 12.

Usage of the microneedle 10 is not limited to being mounted on the syringe barrel 40. A liquid drug may be supplied into the through hole 14*a* of the projection 12 by using a tool other than the syringe barrel 40. Further, the projection 12 may be separated from the base 11 after administration of the liquid drug and left in the skin of the administration target.

The administration target of liquid drug is not limited to a human, but also may be other animals.

Further, the configuration of the above embodiment and the configurations of the modified embodiments can be appropriately combined for use.

Examples

The aforementioned microneedle will be described below by using specific examples and comparative examples.

Examples

As shown in FIG. 5, a mold base having a mold mounted therein was provided. The mold included a fixed mold, a first movable mold, a second movable mold, and a core pin. A projection molding groove of the fixed mold was formed to produce a projection in a quadrangular pyramid shape truncated obliquely to the extending direction thereof as shown in FIG. 1, having a length of the projection of 0.8 mm. A first molding groove of the first movable mold and a second molding groove of the second movable mold are formed to produce a circular support surface. A distal end of the core pin had a cylindrical shape with a diameter of 100 μm. The mold base had a flow path for compression air for cooling, ensuring partial cooling of the fixed mold.

The above mold was mounted in a full automatic injection molding machine (SE18DU, manufactured by Sumitomo Heavy Industries, Ltd.). Polycarbonate heated at 290° C. was injected into the mold at an injection speed of 50 mm/sec, followed by cooling of the mold for a period of 10 seconds. In injection of resin, the amount of compressed air supplied into the flow path in the mold base was adjusted so that a temperature gradient was generated in the fixed mold to thereby control the speed of resin flowing around the distal end of the core pin in the projection molding groove. Molding was performed after the resin used was dried at 120° C. for a period of 8 hours. After the resin was cured, a molded product was taken out from the mold, and then a runner was removed to thereby obtain a microneedle of the example.

In microscopic observation of the microneedle of the example, it was found that a cut extending in a straight line in an extending direction of the projection was formed on a peripheral surface of the projection. This cut, which was a flow path expansion section, had an entire length on a lateral face of the projection of 300 μm.

Further, an area of an opening formed by the through hole on the top face of the projection when the flow path expansion section 14b was closed was $7.9 \times 10^{-3}$ mm$^2$.

Comparative Example

Molding was performed under the same conditions as the above example except that the temperature of the fixed mold was made uniform without supplying compressed air into the flow path in the mold base during injection of resin. Thus, a microneedle of the comparative example was obtained. In microscopic observation of the microneedle of the comparative example, it was found that a cut was not formed in the microneedle.

[Evaluation of Injection Pressure]

The microneedles of the example and comparative example were used to evaluate injection pressure. For each of the microneedles of the example and comparative example, a microneedle was mounted on a syringe barrel, which was filled with saline as a liquid drug, and the projection was then pierced into skin taken from a 12-week-old Wistar rat, followed by injection of 50 μL of saline into the projection. A maximum pressure required for the injection was measured.

As a substitute for a plunger, a tube to which a pressure gauge was connected was inserted into the outer cylinder of the syringe barrel. Then, a gas was supplied into the tube until an inside pressure of the tube reaches a predetermined value. The gas pressure was increased in 0.01 MPa increments until the injection of saline was completed. Thus, a maximum injection pressure was measured.

For each of the example and comparative example, maximum injection pressures in a plurality of samples were measured. The average of maximum injection pressures in the microneedle of the comparative example was 0.12 MPa. On the other hand, the average of maximum injection pressures in the microneedle of the example was 0.08 MPa. That is, it was found that the microneedle of the example allowed for administration of liquid drug at an injection pressure lower than the microneedle of the comparative example, had a through hole which was not susceptible to clogging, and ensured smoother administration of a liquid drug.

REFERENCE SIGNS LIST

10 . . . Microneedle; 11 . . . Base; 11S . . . Support surface; 12, 20, 22, 24 . . . Projection; 13D, 21D, 23D, 25D . . . Lateral face; 13T, 21T, 23T . . . top face; 14a . . . Through hole; 14b, 14c . . . Flow path expansion section; 30 . . . Mold; 31 . . . Fixed mold; 32 . . . First movable mold; 33 . . . Second movable mold; 34 . . . Core pin; 37 . . . Runner; 38 . . . Gate; 40 . . . Syringe barrel; 41 . . . Outer cylinder; 42 . . . Plunger.

What is claimed is:

1. A microneedle, comprising: a base having a support surface; and a projection having a proximal end at the support surface and a distal end that protrudes from the support surface, the projection having a through hole that penetrates the projection in an extending direction of the projection and is open at the distal end, wherein the projection includes a flow path expansion section which is configured to expand a communication path that communicates between an inner space of the through hole and a space surrounding the projection in response to an increase in pressure of a fluid flowing in the through hole, wherein an end of the flow path expansion section is spaced from the support surface as viewed in a direction parallel with the support surface by at least one fifth of a length of the projection to prevent leaking of the fluid onto a skin when the microneedle is used to administer the fluid into the skin.

2. The microneedle of claim 1, wherein the communication path is closed when the fluid does not flow in the through hole.

3. The microneedle of claim 1, wherein
a peripheral surface of the projection includes lateral faces extending from the support surface and a top face connected to the lateral faces, the top face being inclined relative to the support surface,
the through hole is open at the top face, and
a tip of the projection is located on an edge of the top face as viewed in a direction perpendicular to the support surface.

4. The microneedle of claim 3, wherein, the top face is divided into a region closer to the tip of the projection and a region farther from the tip of the projection as viewed in a direction perpendicular to the support surface, the communication path is located in the region farther from the tip.

5. The microneedle of claim 1, wherein
the through hole has an open end that is open at a distal end of the projection, and
the flow path expansion section is a linear portion that extends from the through hole to a peripheral surface of the projection, as well as extending from the open end of the through hole toward the support surface as viewed in a direction parallel with the support surface, and is configured to expand a cut formed at a position of the flow path expansion section as the communication path in response to an increase in pressure of the fluid flowing in the through hole.

6. The microneedle of claim 1, wherein a pressure of the fluid when the flow path expansion section starts to expand the communication path is 0.20 MPa or less.

7. The microneedle of claim 1, wherein an area of an opening formed by the through hole on a peripheral surface of the projection when a fluid does not flow in the through hole is in a range of $5.0 \times 10^{-4}$ mm$^2$ or more and $2.0 \times 10^{-1}$ mm$^2$ or less.

8. The microneedle of claim 1, wherein the end of the flow path expansion section is spaced from the support surface as viewed in the direction parallel with the support surface by at least one third of the length of the projection to prevent leaking of the fluid onto the skin when the microneedle is used to administer the fluid into the skin.

9. The microneedle of claim 1, wherein the base includes an inner space, which extends from a second surface of the base, which is opposite to the support surface of the base, towards the support surface of the base, the through hole of the projection extends from the inner space of the base through the projection, the inner space of the base has a cylindrical wall perpendicular to the second surface of the base, the inner space of the base is configured to be mounted on a cylindrical outer surface of a syringe barrel.

10. The microneedle of claim 1, wherein only one projection protrudes from the support surface of the base.

11. A microneedle, comprising: a base having a support surface; and a single projection having a proximal end at the support surface and a distal end that protrudes from the support surface, the projection having a through hole that penetrates the projection in an extending direction of the projection and is open at the distal end, wherein the projection includes a flow path expansion section which is configured to expand a communication path that communicates between an inner space of the through hole and a space surrounding the projection in response to an increase in pressure of a fluid flowing in the through hole, wherein only one projection protrudes from the support surface of the base.

12. The microneedle of claim 11, wherein the communication path is closed when the fluid does not flow in the through hole.

13. The microneedle of claim 11, wherein
a peripheral surface of the projection includes lateral faces extending from the support surface and a top face connected to the lateral faces, the top face being inclined relative to the support surface,
the through hole is open at the top face, and
a tip of the projection is located on an edge of the top face as viewed in a direction perpendicular to the support surface.

14. The microneedle of claim 13, wherein the top face is divided into a region closer to the tip of the projection and a region farther from the tip of the projection as viewed in a direction perpendicular to the support surface, the communication path is located in the region farther from the tip.

15. The microneedle of claim 11, wherein
the through hole has an open end that is open at a distal end of the projection, and
the flow path expansion section is a linear portion that extends from the through hole to a peripheral surface of the projection, as well as extending from the open end of the through hole toward the support surface as viewed in a direction parallel with the support surface, and is configured to expand a cut formed at a position of the flow path expansion section as the communication path in response to an increase in pressure of the fluid flowing in the through hole.

16. The microneedle of claim 11, wherein a pressure of the fluid when the flow path expansion section starts to expand the communication path is 0.20 MPa or less.

17. The microneedle of claim 11, wherein an area of an opening formed by the through hole on a peripheral surface of the projection when a fluid does not flow in the through hole is in a range of $5.0 \times 10^{-4}$ mm$^2$ or more and $2.0 \times 10^{-1}$ mm$^2$ or less.

18. A microneedle, comprising: a base having a support surface; and a projection having a proximal end at the support surface and a distal end that protrudes from the support surface, the projection having a through hole that penetrates the projection in an extending direction of the projection and is open at the distal end, wherein the projection includes a flow path expansion section which is configured to expand a communication path that communicates between an inner space of the through hole and a space surrounding the projection in response to an increase in pressure of a fluid flowing in the through hole, wherein the base includes an inner space, which extends from a second surface of the base, which is opposite to the support surface of the base, towards the support surface of the base, the through hole of the projection extends from the inner space of the base through the projection, the inner space of the base has a cylindrical wall perpendicular to the second surface of the base, the inner space of the base is configured to be mounted on a cylindrical outer surface of a syringe barrel.

* * * * *